US009526891B2

(12) United States Patent
Eggen et al.

(10) Patent No.: US 9,526,891 B2
(45) Date of Patent: Dec. 27, 2016

(54) INTRACARDIAC MEDICAL DEVICE

(71) Applicant: Medtronic, Inc., Minneapolis, MN (US)

(72) Inventors: Michael D Eggen, Chisago City, MN (US); Vladimir Grubac, Brooklun Park, MN (US); Jean M Carver, Blaine, MN (US); Ryan Goff, Costa Mesa, CA (US); Thomas A Anderson, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/696,141

(22) Filed: Apr. 24, 2015

(65) Prior Publication Data

US 2016/0310723 A1 Oct. 27, 2016

(51) Int. Cl.
*A61N 1/00* (2006.01)
*A61N 1/05* (2006.01)
*A61N 1/362* (2006.01)
*A61M 25/01* (2006.01)

(52) U.S. Cl.
CPC .......... *A61N 1/059* (2013.01); *A61M 25/0147* (2013.01); *A61N 1/362* (2013.01)

(58) Field of Classification Search
CPC .... A61N 1/3756; A61N 1/365; A61N 1/3684; A61N 1/3712; A61N 1/36592; A61N 1/36585; A61N 1/3622
USPC ........................................................ 607/126
See application file for complete search history.

(56) References Cited

U.S. PATENT DOCUMENTS

| 6,652,556 B1 | 11/2003 | VanTassel et al. |
| 6,941,169 B2 | 9/2005 | Pappu |
| 7,149,587 B2 | 12/2006 | Wardle et al. |
| 7,169,164 B2 | 1/2007 | Borillo et al. |
| 8,204,595 B2 | 6/2012 | Pianca et al. |
| 8,433,409 B2 | 4/2013 | Johnson et al. |
| 8,541,131 B2 | 9/2013 | Lund et al. |
| 8,634,912 B2 | 1/2014 | Bornzin et al. |
| 8,634,919 B1 | 1/2014 | Hou et al. |
| 8,670,842 B1 | 3/2014 | Bornzin et al. |
| 8,690,911 B2 | 4/2014 | Miles et al. |
| 8,696,693 B2 | 4/2014 | Najafi et al. |

(Continued)

FOREIGN PATENT DOCUMENTS

| WO | 02/071977 A2 | 9/2002 |
| WO | 2006/065394 A1 | 6/2006 |

OTHER PUBLICATIONS

Eggen, et al., Interventional Medical Systems, Devices, and Methods of Use, U.S. Appl. No. 14/518,261, filed Oct. 20, 2014, 20pp.

(Continued)

*Primary Examiner* — Robert N Wieland
(74) *Attorney, Agent, or Firm* — Evans M. Mburu

(57) ABSTRACT

An implantable pacemaker system includes a housing having a proximal end and a distal end. A control electronics subassembly defines the housing proximal end, and a battery subassembly defines the housing distal end. A distal fixation member extends from the housing distal end for fixing the housing distal end at an implant site. A pacing extension extends from the housing proximal end and carries a pacing cathode electrode. The pacing extension extends the pacing cathode electrode to a pacing site that is spaced apart from the implant site when the pacemaker is deployed in a patient's body.

22 Claims, 11 Drawing Sheets

(56) References Cited

U.S. PATENT DOCUMENTS

| | | | |
|---|---|---|---|
| 8,700,181 B2* | 4/2014 | Bornzin | A61N 1/3756 607/119 |
| 8,781,605 B2 | 7/2014 | Bornzin et al. | |
| 8,795,328 B2 | 8/2014 | Miles et al. | |
| 8,840,641 B2 | 9/2014 | Miles et al. | |
| 8,996,109 B2* | 3/2015 | Karst | A61N 1/36592 607/25 |
| 2004/0147973 A1 | 7/2004 | Hauser | |
| 2009/0082828 A1 | 3/2009 | Ostroff | |
| 2012/0172690 A1 | 7/2012 | Anderson et al. | |
| 2013/0018413 A1 | 1/2013 | Oral et al. | |
| 2013/0110219 A1 | 5/2013 | Bomzin et al. | |
| 2013/0116738 A1 | 5/2013 | Samade et al. | |
| 2013/0116741 A1 | 5/2013 | Bomzin et al. | |
| 2014/0121720 A1 | 5/2014 | Bonner et al. | |
| 2014/0180306 A1 | 6/2014 | Grubac et al. | |
| 2014/0350592 A1 | 11/2014 | Kreidler et al. | |
| 2015/0051616 A1 | 2/2015 | Haasl et al. | |

OTHER PUBLICATIONS

Grubac, et al., Interventional Medical Systems, Devices, and Components Thereof, U.S. Appl. No. 14/518,211, filed Oct. 20, 2014, 25pp.

Anderson, et al., Leadless Pacing System Including Sensing Extension, U.S. Appl. No. 14/694,910, filed Apr. 23, 2015, 31pp.

(PCT/US2016/028288) PCT Notification of Transmittal of the International Search Report and the Written Opinion of the International Searching Authority, mailed Jul. 26, 2016, 11 pages.

* cited by examiner

INTRACARDIAC MEDICAL DEVICE

TECHNICAL FIELD

The disclosure relates to an implantable, wholly intracardiac medical device for delivering cardiac pacing and sensing cardiac signals.

BACKGROUND

Implantable cardiac pacemakers have conventionally been placed in a subcutaneous pocket and coupled to one or more transvenous medical electrical leads carrying pacing and sensing electrodes positioned in a heart chamber, e.g., along an endocardial wall. A cardiac pacemaker implanted subcutaneously may be a single chamber pacemaker coupled to one medical lead for positioning electrodes in one heart chamber, atrial or ventricular, or a dual chamber pacemaker coupled to two leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Leadless intracardiac pacemakers have recently been introduced that are wholly implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves using electrodes carried along the housing of the pacemaker. While single chamber ventricular pacing may adequately address some patient conditions, other conditions may require atrial or dual chamber atrial and ventricular pacing in order to maintain a regular heart rhythm.

SUMMARY

In general, the disclosure is directed to a pacemaker system including an intracardiac pacemaker having a proximal pacing extension that is suitable for implantation wholly within a heart chamber, e.g., within the atrium such as within the atrial appendage.

In one example, the disclosure provides an implantable pacemaker system, comprising a housing having a proximal end and a distal end. The housing includes a control electronics subassembly defining the housing proximal end, a battery subassembly defining the housing distal end, and a distal fixation member extending from the housing distal end for fixing the housing distal end at an implant site. The pacemaker further includes a pacing extension extending from the housing proximal end and comprising an electrical conductor and a pacing cathode electrode carried by the pacing extension. The pacing extension extends the pacing cathode electrode to a pacing site that is spaced apart from the implant site when the pacemaker is deployed in a patient's body.

In another example, the disclosure provides a method comprising deploying a pacemaker housing at an implant site. The pacemaker housing has a proximal end and a distal end and includes a control electronics subassembly defining the housing proximal end and a battery subassembly defining the housing distal end. The method further includes deploying a distal fixation member extending from the housing distal end for fixing the housing distal end at the implant site, and deploying a pacing extension extending from the housing proximal end to position a pacing cathode electrode carried by the pacing extension at a pacing site that is spaced apart from the implant site.

In another example, the disclosure provides an implantable pacemaker system comprising an intracardiac pacemaker and a delivery tool. The pacemaker includes a housing having a proximal end and a distal end including a control electronics subassembly defining the housing proximal end and a battery subassembly defining the housing distal end. The pacemaker further includes a distal fixation member extending from the housing distal end for fixing the housing distal end at an implant site and a pacing extension extending from the housing proximal end. The pacing extension carries a pacing cathode electrode and extends the pacing cathode electrode to a pacing site that is spaced apart from the implant site when the pacemaker is deployed in a patient's body. The delivery tool includes a delivery catheter defining a receptacle for receiving the intracardiac pacemaker and an outer lumen, an inner steering tool extending through the outer lumen and defining an inner lumen, and a steering member extending through the inner lumen and having an engagement member for coupling to the pacing extension for retracting the pacing extension during a surgical procedure.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below

DETAILED DESCRIPTION

Figure 1:
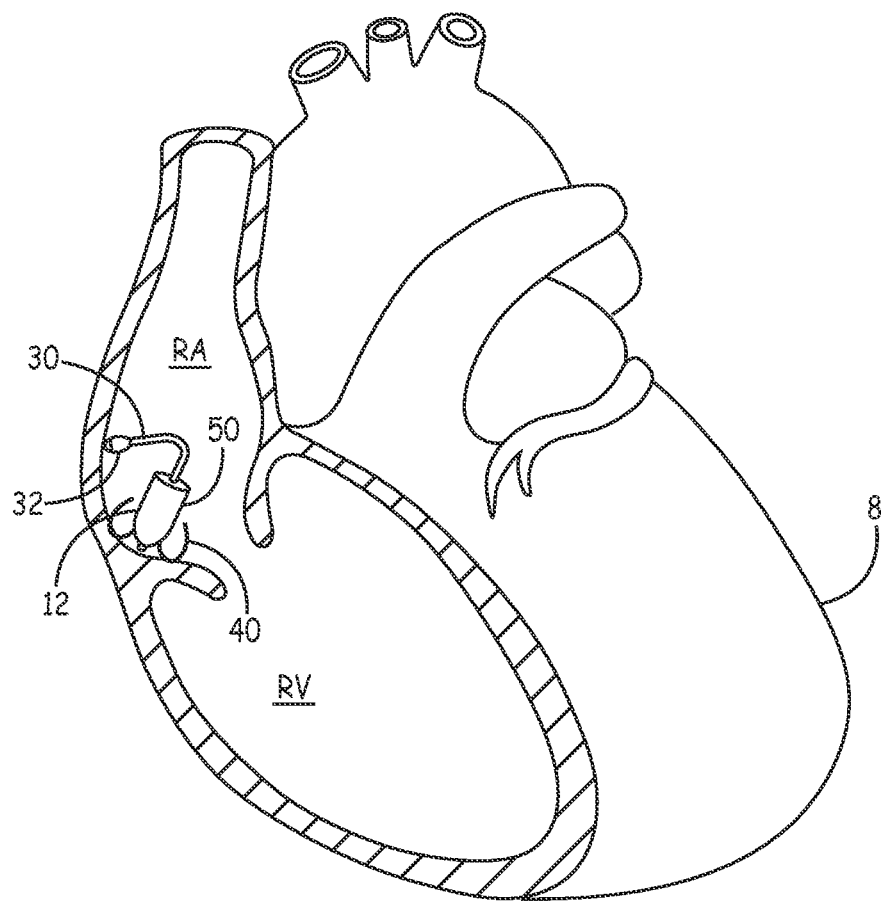
FIG. 1 is a conceptual diagram illustrating an intracardiac pacemaker that may be used to sense cardiac electrical signals and provide therapy to a patient's heart.

FIG. 1 is a conceptual diagram illustrating an intracardiac pacemaker 12 that may be used to sense cardiac electrical signals and provide therapy to a patient's heart 8. Pacemaker 12 is shown positioned in the right atrium (RA) of a patient's heart but may be positioned in the RA or the left atrium, or a ventricular chamber in various examples. Pacemaker 12 includes a proximal pacing extension 30 extending from a proximal end of housing 50 of pacemaker 12 and carrying a proximal pacing electrode 32. In some examples, pacemaker 12 is configured for implantation in an atrial chamber such that housing 50 is positioned in an atrial appendage.

Pacemaker 12 is configured to sense cardiac electrical signals, e.g., an intracardiac electrogram (EGM), and deliver pacing pulses via a pair of electrodes including proximal pacing electrode 32. Pacemaker 12 may include a distal fixation member 40 to stably maintain an implant position of pacemaker 12 in a desired location, e.g., within a right atrium or within a left atrium and more specifically within a right atrial appendage or a left atrial appendage. Proximal pacing extension 30 may extend from the housing 50 to position proximal pace electrode 32 at a targeted pacing site, which may be within the atrial chamber or the atrial appendage but is spaced apart from the implant site of distal fixation member 40.

Pacemaker 12 is reduced in size to enable an intracardiac implantation and may be generally cylindrical in shape to enable transvenous implantation of pacemaker 12 via a delivery catheter. It is recognized that pacemaker 12 may be capable of bidirectional wireless communication with an external device, such as a programmer used by a clinician or other user in a medical facility, a home monitor located in a patient's home, or a handheld device. An external device may be used to program sensing and therapy delivery control parameters in pacemaker 12.

Figure 2:
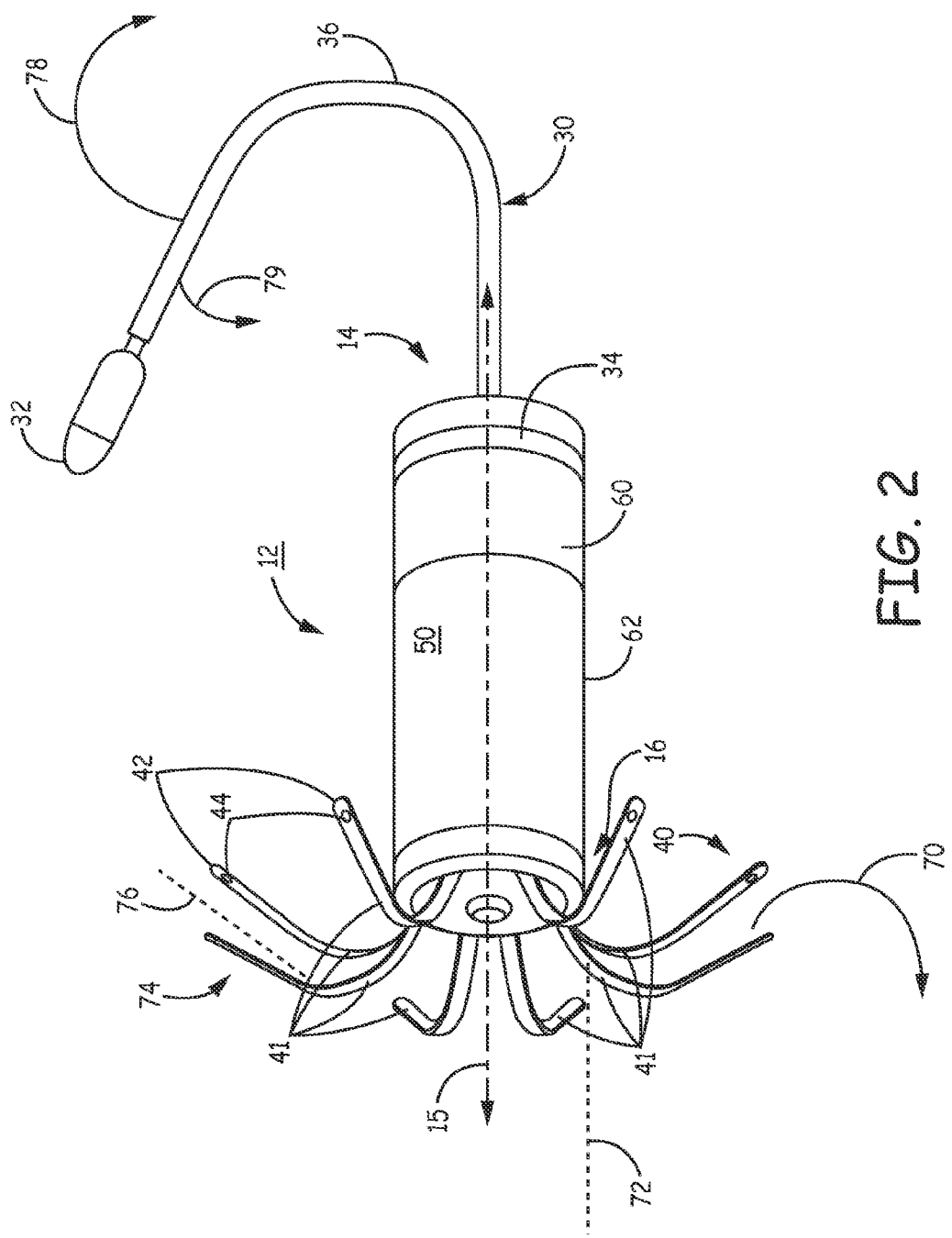
FIG. 2 is a conceptual diagram of the intracardiac pacemaker shown in FIG. 1.

FIG. 2 is a conceptual diagram of intracardiac pacemaker 12 shown in FIG. 1. Pacemaker 12 includes a housing 50 having a proximal end 14 and a distal end 16 and proximal pacing extension 30 extending from the housing proximal end 14. The housing distal end 16 is referred to as "distal" because it is expected to be the leading end delivered first through a delivery tool or catheter and will be the housing end that is anchored to heart tissue via fixation member 40 at a housing implant site. Proximal housing end 14 is referred to as "proximal" because it is located proximally during delivery of pacemaker 12 as it is advanced through a delivery tool and does not become anchored at an implant site but will generally extend into the blood pool of the heart chamber in which pacemaker 12 is implanted. Proximal and distal housing ends 14 and 16 are shown to be substantially flat portions of housing 50, but one or both ends 14 and 16 may be rounded, substantially hemispherical, cone-shaped or tapered in other examples.

Housing 50 includes a control electronics subassembly 60 that is assembled with a battery subassembly 62. Control electronics subassembly 60 houses the electronics for sensing cardiac signals, producing pacing pulses and controlling therapy delivery and other functions of pacemaker 12. Battery subassembly 62 provides power to control electronics subassembly 60. Battery subassembly 62 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety. Control electronics subassembly 60 defines the housing proximal end 14 and battery subassembly defines the housing distal end 16. In this way, proximal pacing extension 30 may be electrically coupled to electronics within control electronics subassembly 60 to provide electrical connection between proximal pacing electrode 32 and electronics enclosed by control electronics subassembly 60 via an electrical feedthrough (not illustrated) crossing housing 50.

Distal fixation member 40 may include multiple fixation tines 41 projecting from distal housing end 16 to stably maintain distal housing end 16 at an implant site within a heart chamber. Fixation member tines 41 are shown arranged along a periphery of the housing distal end 16, along battery subassembly 62. Each of fixation tines 41 may extend in a generally distal direction from a fixed tine end coupled to distal housing end 16, then curve or bend laterally and proximally to extend the free, terminal tine end 42 in a relatively radial and proximal direction with respect to distal housing end 16. The fixation member 40 may be a passive fixation member having distal tine ends 42 that are non-penetrating, non-piercing ends such that the individual tines 41 passively interact with tissue at the implant site, e.g., the atrial pectinate muscles or the ventricular trabeculae, to maintain a stable position of housing 50. Fixation member tines 41 may hold distal housing end 16 at an implant site by being wedged between opposing tissue surfaces at the implant site, e.g., between opposing endocardial walls of the right atrial appendage or left atrial appendage.

Fixation member tines 41 may be elastically deformed between an extended position and compressed position, having a relaxed position intermediate the extended and compressed positions as shown in FIG. 2. During implantation, pacemaker 12 may be placed within a lumen of a delivery tool such that fixation member tines 41 are held in a distally extended position. In the extended position, the fixation member tines 41 are straightened distally as indicated by arrow 70 toward a position 72 approximately in alignment with and surrounding central axis 15 of pacemaker 12. Upon release from the delivery tool, the fixation member tines 41 regain the relaxed position as shown, becoming engaged with tissue such as the atrial pectinate muscles or the ventricular trabeculae at the implant site. At some implant locations, such as within an atrial appendage, the fixation member tines 41 may become wedged between opposing tissue surfaces such that tines 41 are pressed inward toward central axis 15, as generally indicated by arrow 74 to a compressed position, e.g., as indicated by dashed line 76. Lateral pressure caused by elastically deformed tines 41 maintains the housing 50 at the implant site in some applications.

Fixation member 40 may be formed from a biocompatible polymer, e.g., polyurethane, silicone, polyethylene, or polyether ether ketone (PEEK). In some examples, fixation member 40 includes a shape memory material such as nitinol to retain a pre-formed bend or curve that is straightened when pacemaker 12 is placed in a delivery catheter or tool and restored after pacemaker 12 is released from the delivery catheter or tool. Each fixation member tine 41 may be elastically deformable between a relaxed condition (as shown) and an extended condition. In the example shown, each tine 41 includes a radio-opaque marker 44 that is visible under fluoroscopy or x-ray and facilitates delivery of pacemaker 12 to a desired implant site and confirmation of fixation at a targeted site. Fixation member 40 extending from battery subassembly 62 may generally correspond to examples of a fixation member assembly disclosed in commonly-assigned U.S. patent application Ser. No. 14/518,261 (Eggen, et al.), incorporated herein by reference in its entirety.

A proximal, pacing cathode electrode 32 is carried by proximal pacing extension 30 extending from housing proximal end 14. A distal, anode electrode 34 may be provided as a ring electrode along housing 50, e.g., near housing proximal end 14 or anywhere along housing 50. Distal electrode 34 may be an uninsulated portion of housing 50 or electrically coupled to housing 50 to serve as an anode return electrode of a bipolar pacing and sensing electrode pair including electrodes 32 and 34. Electrode 32, which may be a tip electrode, is provided as the cathode electrode for delivering pacing pulses and sensing EGM signals and is coupled to a pulse generator and sensing module enclosed in control electronics subassembly 60 via an electrical conductor extending within pacing extension 30.

Proximal pacing extension 30 includes an electrically-insulating elongated body 36 through which an electrically conductive member, e.g., a wire or cable, extends from an electrical feedthrough that provides electrical coupling across housing 50 from internal electronics to electrode 32. Electrode 32 is electrically coupled via the feedthrough to circuitry included in control electronics subassembly 60. For example, electrode 32 serves as a cathode electrode for delivering pacing pulses and is therefore coupled to a pulse generator included in control electronics subassembly 60 while housing-based ring electrode 34 is coupled to housing 50 and serves as a return anode. Proximal pacing electrode 32 may also be coupled to a sensing module for sensing an EGM signal in combination with housing-based electrode 34. The proximal pacing electrode 32 is extended at a targeted pacing site by pacing extension 30, and housing 50 may be passively fixed by fixation member 40 at an implant site that is spaced apart from the targeted pacing site. Both the pacing site and the implant site may be within the same heart chamber but are spaced apart such that the pacing site is not influenced by scar tissue or tissue encapsulation that may develop at the implant site due to interaction of the fixation member 40 at the implant site.

Electrodes 32 and 34 may include, without limitation, titanium, platinum, iridium or alloys thereof and may include low polarizing coatings, such as titanium nitride, iridium oxide, ruthenium oxide, platinum black, among others. Housing 50 may be formed from a biocompatible material, such as a stainless steel or titanium alloy. In some examples, the housing 50 includes an insulating coating. Examples of insulating coatings include parylene, urethane, PEEK, or polyimide among others. The entirety of the housing 50 may be insulated, but only electrode 34 uninsulated. In other examples, the entirety of the housing 50 may function as a return electrode instead of providing a localized electrode 34.

Proximal pacing extension 30 comprises materials that permit elongated body 36 to substantially maintain its position relative to housing 50 such that electrode 32 is maintained at the target pacing site, even in the presence of gravity, surrounding blood flow and heart motion. For example, elongated body 36 may have a bending stiffness of about 1.6 Newtons-square millimeter (Nmm$^2$), or $1.6 \times 10^{-6}$ N-m$^2$, though other bending stiffness values may be used. Proximal pacing extension 30 is configured to passively position electrode 32 at a location away from the implant site. The implant site of housing distal end 16 and the target pacing site of electrode 32, however, may be within the same chamber of the heart 8. For example, housing distal end 16 may be implanted within the right atrial appendage and electrode 32 may be positioned at a target pacing site within the right atrial appendage or the right atrium. Proximal pacing extension 30 may have sufficient rigidity (e.g., stiffness) to permit elongated body 36 to extend away from housing 50, even as blood moves around elongated body 36 within the chamber of the heart.

Proximal pacing extension 30 may include a pre-formed bend or curved shape as shown in FIG. 2 to facilitate positioning of electrode 32 at a target pacing site. Proximal pacing extension body 36 may be deformable to alter the shape of the bend or curve. For example, the pre-formed relaxed position may be adjustable by a clinician to enable proximal tip electrode 32 to be positioned at different positions relative to housing 50, e.g., at different angular positions and distances from housing proximal end 14.

In some cases, body 36 is elastically deformable in the direction generally indicated by arrow 78 to an extended, i.e., substantially straight, position, e.g., approximately aligned with pacemaker longitudinal central axis 15. Pacemaker 12 may be placed in a delivery tool having a central lumen such that proximal pacing extension 30 extends proximally within the central lumen in an extended position when the housing 50 and fixation member 40 are positioned in a distal receptacle of the delivery tool that retains housing 50 and fixation member 40 until pacemaker 12 is deployed from the delivery tool, as described below. Upon release from the delivery tool, proximal pacing extension 30 resumes its pre-formed, relaxed shape.

In other examples, proximal pacing extension 30 may be elastically deformed into a compressed position, as indicated by arrow 79, which allows proximal pacing extension 30 to be in a substantially folded position while retained within a delivery tool. Upon deployment from the delivery tool, the proximal pacing extension 30 resumes its pre-formed relaxed position.

In various examples, pacing extension 30 may have a relaxed position that is straight or curved at any desired angle according to a particular pacing application. For example pacing extension may curve between zero degrees (straight) and nearly 180 degrees so that proximal pacing electrode 32 is facing approximately the same direction as housing distal end 16. In other words, the proximal portion of pacing extension 30 carrying proximal pacing electrode 32 may extend nearly parallel to the distal portion of pacing extension 30 that extends away from housing proximal end 14. Proximal pacing extension may vary in length between embodiments and may be, for example with no limitation intended, between 1 cm and 10 cm in length.

Proximal pacing extension 30 may include a coiled or stranded wire or cable conductor that extends from proximal tip electrode 32 through elongated body 36. The combination of the polymer material of elongated body 36 and the electrically conductive wire or cable extending there through may provide sufficient stiffness to proximal pacing extension 30 to enable conductor 30 to be self-supporting and substantially maintain its position relative to housing 50. In other examples, proximal pacing extension 30 may include a stiffening member as generally disclosed in U.S. patent application Ser. No. 14/694,910, filed on Apr. 23, 2015, incorporated herein by reference in its entirety. Thus proximal pacing extension 30 may be a self-supporting body having a stiffness and shape defined by an electrically conductive wire or cable (not illustrated), a stiffening sleeve surrounding the wire or cable (not illustrated), and/or a stiffening member (not illustrated), which may extend through the center of a coiled electrically conductive wire or cable.

Figure 3A:
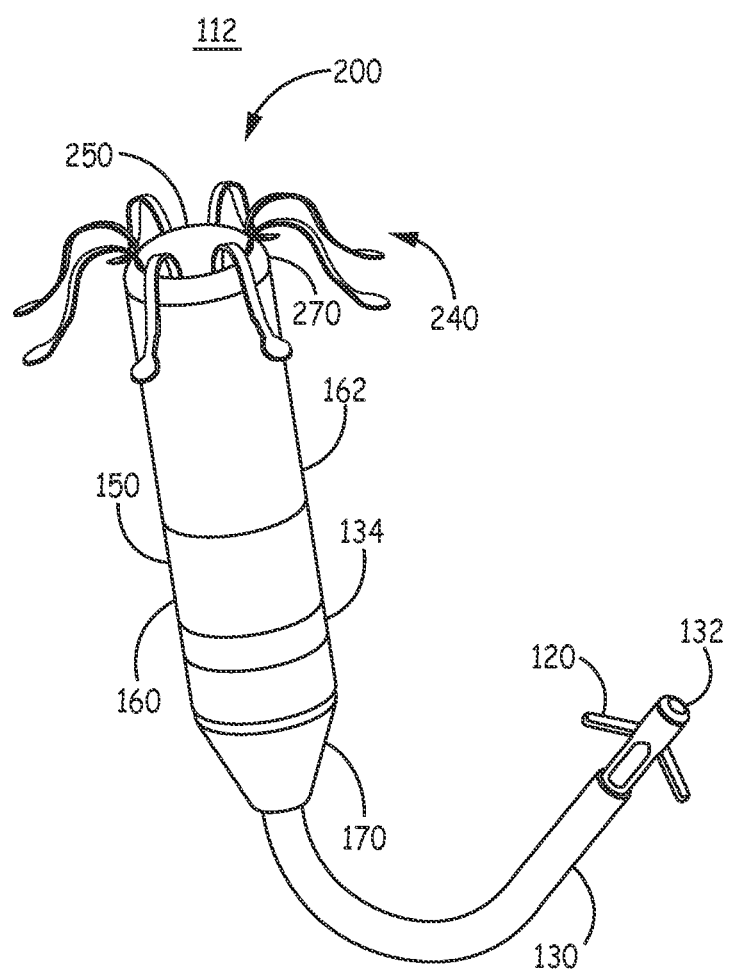
FIG. 3A is a conceptual diagram of a pacemaker according to another example.

FIG. 3A is a conceptual diagram of a pacemaker 112 according to another example. In this example, the proximal pacing extension 130 includes a proximal passive fixation member 120 near the proximal pacing tip electrode 132 to passively anchor pacing tip electrode 132 at a desired pacing site. Fixation member 120 may include one or more passive fixation tines for passively interacting with tissue at the pacing site. Proximal pacing extension 130 may be a self-supporting extension as described above to contribute to maintaining a position of proximal pacing tip electrode 132 at a pacing site. Alternatively, proximal pacing extension 130 may be a flexible pacing extension that flexes to absorb relative movement between distal fixation member 240 and proximal fixation member 120. In this case proximal fixation member 120 maintains the position of proximal pacing electrode 132, and the flexion of proximal pacing extension 130 may absorb forces due to heart motion that might otherwise act on distal fixation member 240 and/or proximal fixation member 120 and cause dislodgement of pacemaker 112 from desired implant and pacing sites, respectively.

Pacing tip electrode 132 functions as the pacing cathode electrode and ring electrode 134, shown along pacemaker housing 150, serves as the return anode electrode. As indicated above, anode ring electrode 134 may be positioned anywhere along battery subassembly 162 or control electronics subassembly 160.

Pacemaker 112 includes a proximal extension coupling member 170 that facilitates hermetic coupling of proximal pacing extension 130 and strain relief at the coupling site between housing 150 and pacing extension 130. Coupling member 170 may additionally provide a relatively smooth outer contour of pacemaker 112 to eliminate corners or edges that might otherwise cause tissue irritation.

Pacemaker 112 includes a distal fixation member subassembly 200 coupled to the distal end of battery subassembly 162. Distal fixation member subassembly 200, which is described in greater detail in conjunction with FIGS. 4A and 4B, includes distal fixation member 240, a distal cap 250 and coupling ring 270. Assembly of housing fixation member 240 at the pacemaker distal end, with pacing extension 130 extending from the pacemaker proximal end, enables pacing tip electrode 132 to be anchored at a desired pacing site away from the implant site of fixation member 240 such that both the pacing cathode electrode 132 and the anode ring electrode 134 are positioned away from the fixation member 240 that anchors housing 150 at the housing implant site. In this way, tissue encapsulation that forms along fixation member 240 will not influence pacing capture thresholds.

Figure 3B:
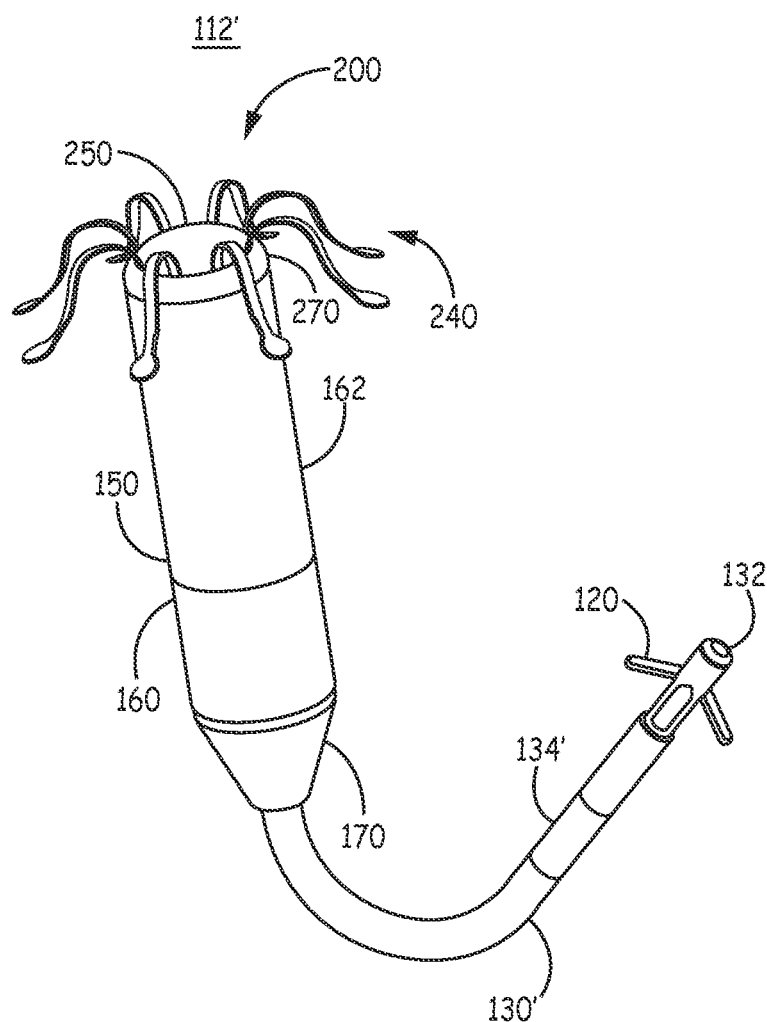
FIG. 3B is a conceptual perspective view of a pacemaker according to another example.

FIG. 3B is a conceptual perspective view of pacemaker 112' according to another example. Pacemaker 112' corresponds to pacemaker 112 except that a return anode ring electrode 134' is carried by pacing extension 130', which may be in place of or in addition to the ring electrode 134 positioned along housing 150 as shown in FIG. 3A. In this case, pacing extension 130' includes insulated conductors extending from each of respective electrodes 132 and 134 to pacemaker housing 150. Anode ring electrode 134' may be coupled to the housing 150 and cathode tip electrode 132 may be coupled to internal circuitry, e.g., a pacing pulse generator and a sensing module, included in control electronics subassembly 160 via an electrical feedthrough.

Figure 4A:
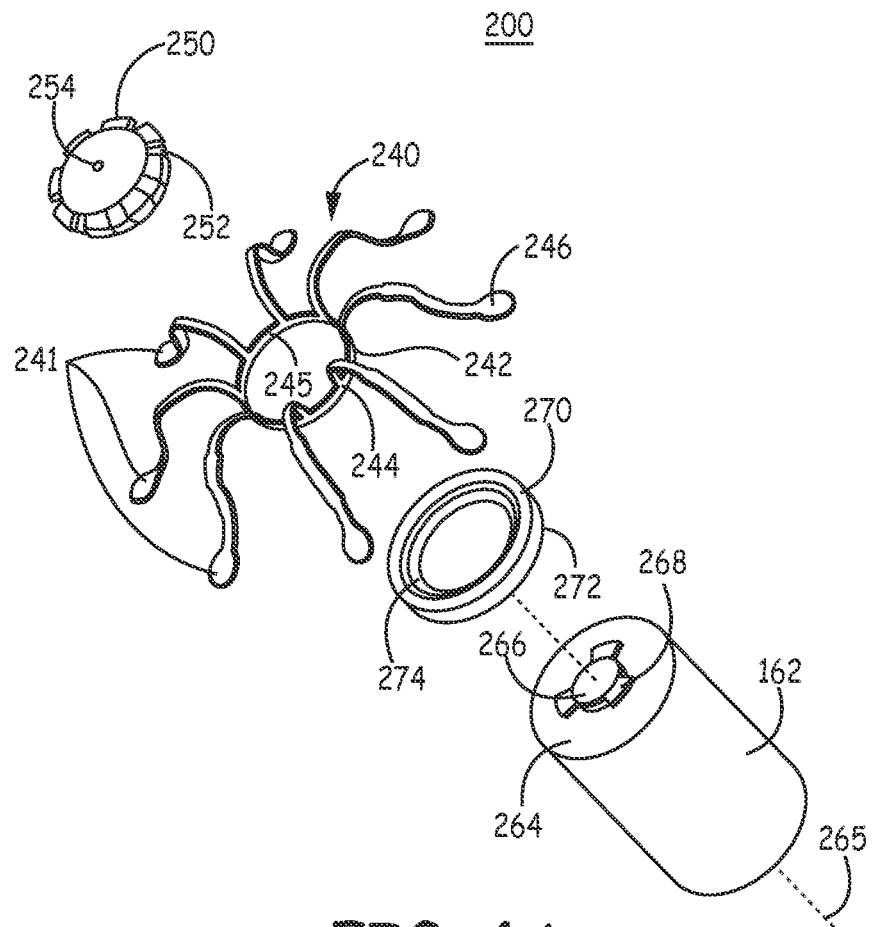
FIG. 4A is an exploded perspective view of a pacemaker distal fixation member subassembly and a battery subassembly.

FIG. 4A is an exploded perspective view of a distal fixation member subassembly 200 and battery subassembly 162 that may define the distal portion of the pacemaker 112 of FIG. 3A or other examples of pacemakers having a distal housing fixation member and proximal pacing extension as described herein. Distal fixation member subassembly 200 includes fixation member 240, a distal cap 250, and a coupling ring 270. Battery subassembly 162 has a distal face 264 including a cap mating member 266 protruding longitudinally from distal face 264 for centering and mating with distal cap 250. Cap mating member 266 is shown to be symmetrically centered on a central axis 265 of battery subassembly 162 but may be centered off the central axis 265 and/or be asymmetrical in other examples and still provide a guide for alignment and proper connection with fixation member 240 and cap 250.

Cap mating member 266 may include one or more radially-extending alignment members 268 that guide proper alignment with a corresponding mating feature of cap 250. Alignment members 268 are shown as three protruding tabs in FIG. 4A, but cap mating member 266 may include less than three or more than three alignment features in other examples, which may include radially protruding features, such as a tab or flange, or radially intruding features, such as a groove, notch or channel.

Figure 4B:
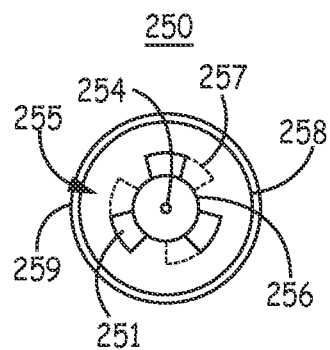
FIG. 4B is a bottom view of a distal cap of the distal fixation member assembly of FIG. 4A.

FIG. 4B is a bottom view of distal cap 250 showing a proximal, mating surface 255 of cap 250 that interfaces with distal face 264 and cap mating member 266 of battery subassembly 162. Distal cap 250 further includes a female mating feature 256 having a geometry that matches the geometry of cap mating member 266 of battery subassembly 162. In the example shown, distal cap 250 has a female mating feature 256 including open receptacles 251 for receiving radially-extending alignment features 268 of a male cap mating member 266 protruding from battery subassembly 162.

With continued reference to FIG. 4A, fixation member 240 includes a tine ring 242 and multiple fixation tines 241 extending therefrom. Fixed ends 244 of the fixation tines 241 are attached to tine ring 242 such that free ends 246 of fixation tines 241 extend outwardly from tine ring 242. Tine ring 242 is sized for insertion along an interior diameter 274 of coupling ring 270. Coupling ring 270 may be configured to mate with battery subassembly distal face 264 in a butt or interlocking joint such that the outer circumference 272 of coupling ring 270 forms a smooth continuous surface with the exterior surface of battery subassembly 162 (as shown in FIGS. 3A and 3B).

Distal cap 250 includes a peripheral flange 259 (FIG. 4B) that defines a peripheral circumferential ridge 258 for insertion along the inner diameter 245 of tine ring 242. The outer diameter of peripheral circumferential ridge 258 is sized to fit within coupling ring 270 and distal cap flange 259 may extend over and conceal tine ring 242 after assembly, e.g., as shown in FIGS. 3A and 3B.

The female mating feature 256 of distal cap 250 (shown in FIG. 4B) receives cap mating member 266 of battery subassembly 162, trapping fixation member 240 and coupling ring 270 there between. A medical grade adhesive, such as silicone adhesive, is injected through a fill port 254 that is open to the exterior surface of cap 250 as shown in FIG. 4A. The medical adhesive fixedly couples distal cap 250 to battery subassembly 162, thereby securing distal fixation member subassembly 200, including fixation member 240, to the battery subassembly 162.

In some examples, distal cap 250 includes interior retaining grooves 257 that interlock and hold cap mating member 266 when distal cap 250 is rotated with respect to battery subassembly 162. Retaining grooves 257 extend interiorly within cap 250 from female mating feature 256 for receiving radially-extending alignment features 268 upon rotation of cap 250. After rotation, interlocking grooves 257 retain cap mating member 266 so that fixation member subassembly 200 remains securely assembled with battery subassembly 162. Medical grade adhesive may be injected through fill port 254 to back fill open receptacles 251 of female mating feature 256 after rotation of cap 250 positions radially-extending alignment features 268 within interlocking grooves 257. The adhesive provides permanent coupling of fixation member subassembly 200 to battery subassembly 162.

In the example shown, cap mating member 266 of battery 162 is a protruding, male member having a geometry configured to mate with a female mating feature 256 of cap 250. It is recognized that in alternative examples the battery subassembly 162 may include a female mating feature on distal face 264 and distal cap 250 may have a protruding, male mating member that is inserted into the female mating feature on distal face 264.

Figure 5:
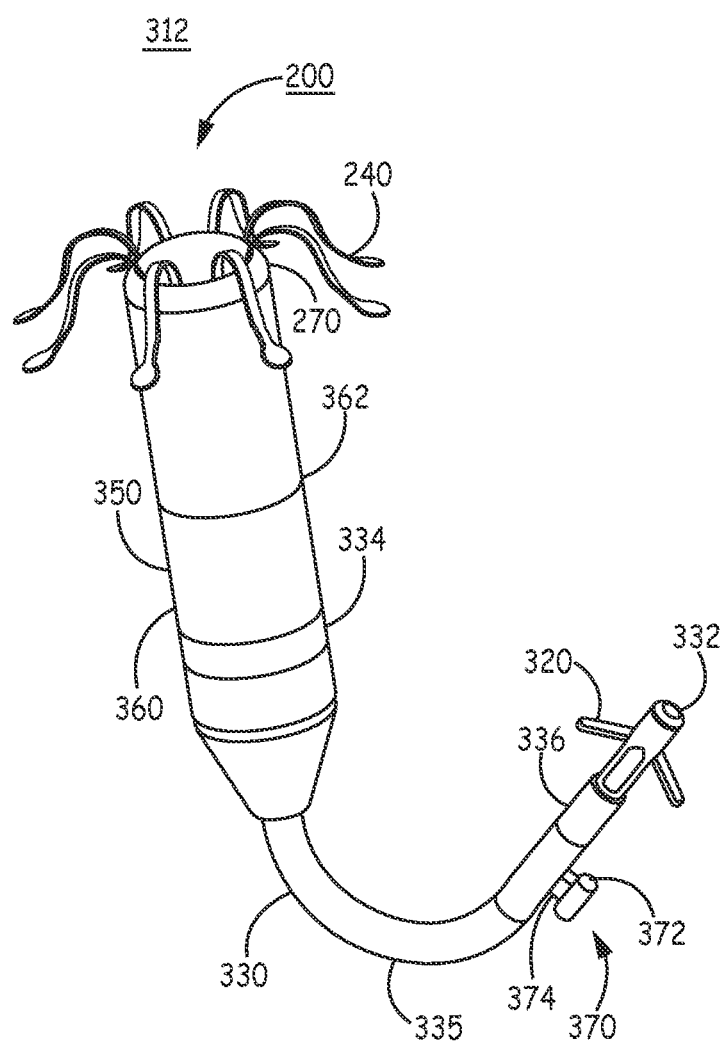
FIG. 5 is a conceptual diagram of a pacemaker having a proximal pacing extension with a steering member attachment member.

FIG. 5 is a conceptual diagram of a pacemaker 312 having a proximal pacing extension 330 with a steering member attachment member 370. Pacemaker 312 may include distal fixation subassembly 200 as described in conjunction with FIGS. 4A and 4B, a pacemaker housing 350 including a proximal portion defined by control electronics subassembly 360 and a distal portion defined by battery subassembly 362, and an anode ring electrode 334 along housing 350.

Pacing extension 330 includes a proximal pacing tip electrode 332 and may include a passive fixation member 320. Pacing extension 330 may be a self-supporting extension to support a position of pacing tip electrode 332 at a pacing site that is spaced apart from the implant site at which housing fixation member 240 is implanted. Alternatively, pacing extension 330 may be flexible to absorb relative movement between distal fixation member 240 and proximal fixation member 320.

The pacing site at which proximal pacing electrode 332 is positioned may be selected by adjusting the position of pacing tip electrode 332 by actively steering pacing extension 330 using a detachable steering member that is removably coupled to pacing extension 330 via attachment member 370. Attachment member 370 includes a rail 374 extending radially from elongated body 336 of pacing extension 330 and a longitudinal post 372 coupled to the rail 374. Attachment member 370 is spaced distally from proximal tip electrode 332, but relatively closer to proximal tip electrode 332 than to housing 350. In some examples, attachment member 370 is positioned between proximal tip electrode 332 and a pre-formed curve 335 of elongated body 336 of pacing extension 330.

In other examples, fixation member 320 may also serve as an attachment member which a steering member loop may be removably coupled. A snare-type or tether-type loop of a steering member, e.g., steering member 380 of FIG. 6A or steering member 480 of FIG. 7A described below, may encircle or be tightened around a tine of fixation member 320 or fixation member 320 may be configured with an eye, loop or hook through which a steering member loop may extend.

Figure 6A:
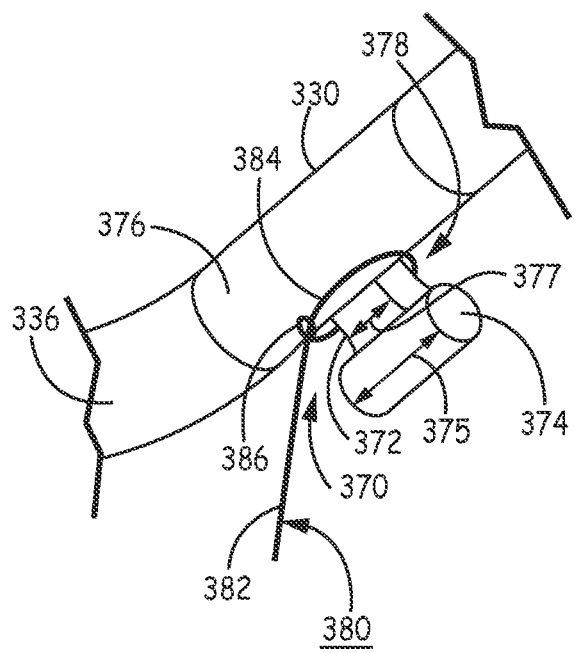
FIG. 6A is an enlarged view of the attachment member of FIG. 5.

FIG. 6A is an enlarged view of attachment member 370. Rail 372 extends from elongated body 336 of pacing extension 330. In some examples, attachment member 370 includes a sleeve 376 that extends around elongated body 336 or forms a segment of elongated body 336. Sleeve 376, rail 374 and post 372 may be a single piece part that is molded from a medical grade, biocompatible polymer, such as polyurethane, silicone, polyethylene, or polyether ether ketone (PEEK) or a machined part formed from metal, e.g., titanium, stainless steel, platinum, or alloys thereof. All or a portion of attachment member 370 may include a radiopaque material that is visible under fluoroscopy for guidance during implantation and/or verification of an implant position. In one example, attachment member 370 includes a metal portion that is overmolded by polyurethane and is visible under radiographic or fluoroscopic imaging. When sleeve 376 is used, it may be formed of a material to approximately match the compliance of body 336.

Figure 6B:
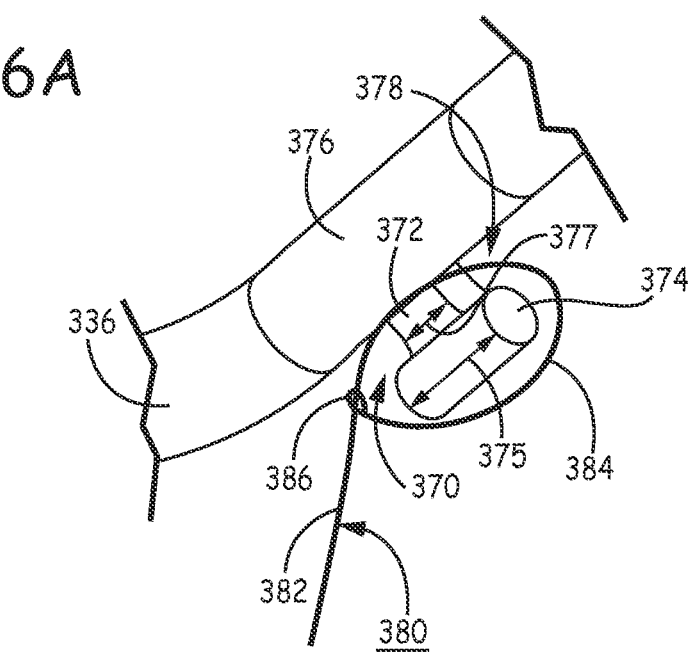
FIG. 6B is a conceptual diagram of a steering member as it is removed from the attachment member of FIG. 6A.

In other examples, rail 372 may be attached or bonded to elongated body 336 by an adhesive or other coupling material and may be formed from a polymer material or polymer-coated metal wire. Rail 372 may extend through the outer insulation of elongated body 336 of proximal pacing extension 330 to form a mechanical joint between attachment member 370 and body 336 that may be sealed and reinforced with a medical adhesive. In FIGS. 6A and 6B, post 374 is shown to run longitudinally (parallel) along elongated body 336. In other examples, post 374 could be arranged at other angles or generally perpendicular to elongated body 336.

A steering member 380 includes a steering body 382 and an engagement member 384 configured to engage attachment member 370 to thereby removably couple steering member 380 to proximal pacing extension 330. In the example, of FIG. 6A, engagement member 384 is shown as, and also referred to herein as, a snare loop 384 formed by extending steering body 382 through snare eye 386. Post 374 has a post height 375 that is greater than rail height 377 such that post 374 and sleeve 376 (or body 336 when sleeve 376 is not used) define a gap 378 in which snare loop 384 is retained by post 374 when snare loop 384 is tightened around rail 372 by retraction of steering body 382 through snare eye 386. In this steering position of steering member 380, manipulation of a proximal end (not shown in FIG. 6A) of steering body 382 by an implanting clinician results in movement of the proximal pacing electrode 332 (seen in FIG. 5). Snare loop 384 may be positioned and tightened around rail 372 during manufacturing such that steering member 380 comes pre-assembled with pacemaker 312, which may be pre-loaded in a delivery tool. In other examples, the implanting clinician may attach steering member 380 to attachment member 370 at the time of the implant procedure.

Proximal pacing electrode 332 can be moved to various candidate pacing sites by manipulating steering body 382 when snare loop 384 is coupled to attachment member 370. Pacing capture threshold, impedance measurement, therapy response, or other testing at the candidate pacing site may be performed to determine if a response to pacing at a candidate pacing site elicits a desired pacing response. Proximal pacing electrode 332 may be repositioned using steering member 380, e.g., by retraction and advancement of steering body 382 and/or rotation of steering body 382, until an acceptable pacing site is identified.

FIG. 6B is a conceptual diagram of steering member 380 as it is removed from attachment member 370. Once a desirable pacing site is identified, steering member 380 is removed from attachment member 370 by releasing tension and advancing a proximal end of steering body 384 (through snare eye 386) such that snare loop 384 enlarges to a diameter greater than post height 375. Snare loop 384 slips over post 374, and steering member 380 is retracted and withdrawn, leaving pacing tip electrode 332 positioned at the selected pacing site.

Figure 7A:
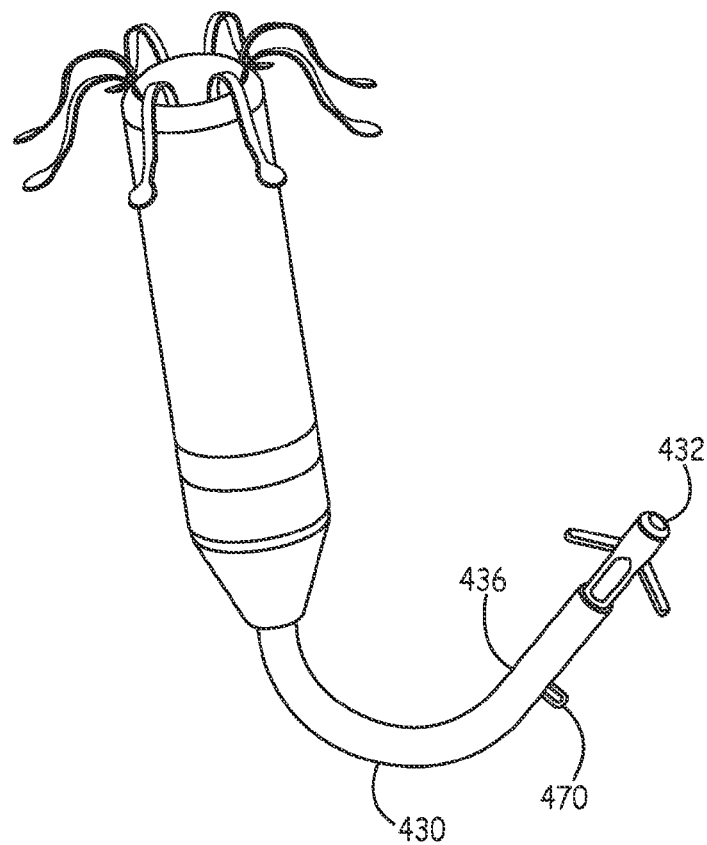
FIG. 7A is a perspective view of a pacemaker according to another example.

FIG. 7A is a perspective view of a pacemaker 412 according to another example. Pacemaker 412 corresponds to pacemaker 312 shown in FIG. 5 but instead of attachment member 370 having the post and rail arrangement shown in FIGS. 6A and 6B, attachment member 470 of pacemaker 412 is a loop. In various examples, attachment member 470 may include a post, rail, hook, loop, ring, groove, channel, notch or other feature configured to receive an engagement member of a steering member. Attachment member 470 may generally include any of the constructions described above including, but not limited to, a molded or machined part that is adhesively and/or mechanically coupled to body 436 of pacing extension 430. Attachment member 470 may be a polymeric material or polymer-coated wire and may be coupled to the external surface of body 436, coupled to a sleeve member around body 436 or inserted as a segment of body 436, and/or extend through the outer insulation of body 436 to form a mechanical joint with body 436, which may be adhesively sealed.

Figure 7B:
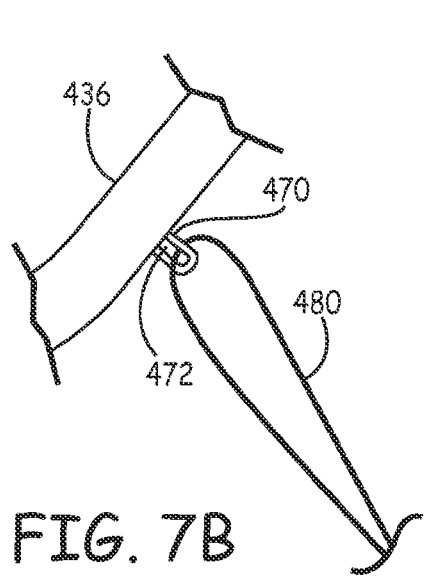
FIG. 7B is an enlarged view of a portion of the pacing extension of the pacemaker of FIG. 7A.

FIG. 7B is an enlarged view of pacing extension elongated body 436 and attachment member 470. Attachment member 470 is shown as a "U" shaped loop extending radially from elongated body 436 and defining an opening 472 through which a steering member 480 extends. Attachment member 470 may be a loop, ring, or eye that encircles an opening for the steering member 480 to be threaded through and may extend directly from elongated body 436 or be attached to a rail extending from elongated body 436.

Steering member 480 may be a stylet, pull wire, suture or other elongated body having a diameter small enough to be threaded through attachment member 470. Pacemaker 412 may be packaged at a manufacturing facility with steering member 480 already threaded through attachment member 470, or an implanting clinician may thread the steering member 480 at the time of the implant procedure. Steering member 480 is looped through attachment member 470 such that two proximal ends (not shown in FIG. 7B) of steering member 480 extend to a proximal handle of a delivery tool to enable retraction of the steering member proximal ends for manipulation of the pacing extension 430. Retraction, advancement, and/or rotation of the proximal ends of steering member 480 may alter the position of proximal pacing electrode 432 enabling testing at different candidate pacing sites. Steering member 480 in this example forms an elongated loop that captures attachment member 470 and extends from attachment member 470 to the a proximal end of the delivery tool where at least one of the two proximal ends is exposed for retraction and/or rotation of steering member 480.

Figure 7C:
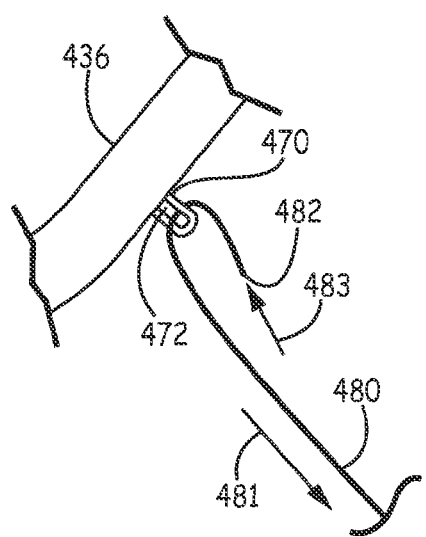
FIG. 7C is an enlarged perspective view of the steering member of FIG. 7B being removed from the attachment member of the proximal pacing extension.

FIG. 7C is an enlarged perspective view of steering member 480 being removed from attachment member 470. After the pacing site is selected and proximal tip electrode 432 is acceptably positioned at the selected pacing site, one proximal end 482 of steering member 480 is released and the other proximal end (not shown in FIG. 7C) is retracted (as generally indicated by arrow 481) to advance proximal end 482 (as generally indicated by arrow 483) through a delivery tool lumen and through attachment member 470. Advancement of proximal end 482 through a delivery tool and through and out of attachment member 470 enables removal of steering member 480 from attachment member 470. In this way, steering member 480 is released from attachment member 470 and can be fully removed from the patient.

Figure 8:
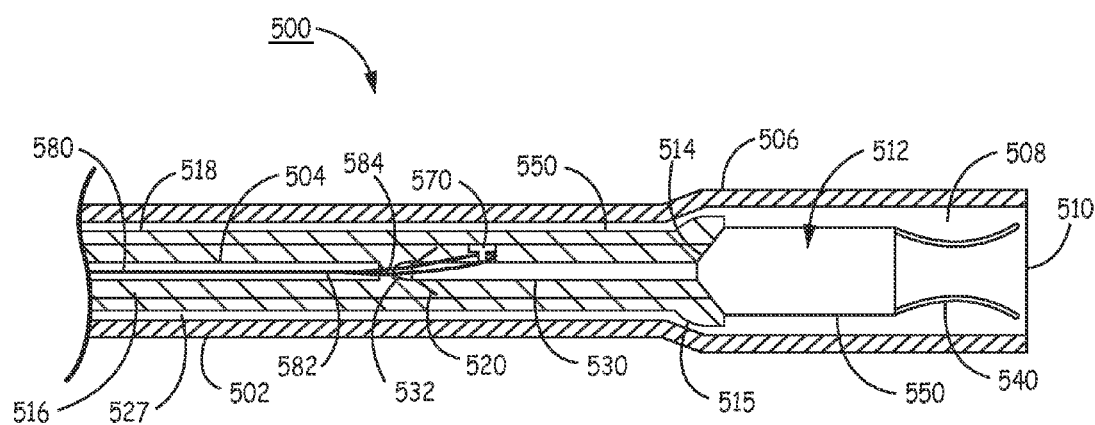
FIG. 8 is a sectional view of a distal portion of a delivery tool and a pacemaker according to one example.

FIG. 8 is a sectional view of a distal portion of a delivery tool 500 and a pacemaker 512 according to one example. Delivery tool 500 includes an outer delivery catheter 502, advancement tool 518, and inner steering tool 504. Outer delivery catheter 502 has a distal device receptacle 506 that defines a distal cavity 508 for receiving and retaining pacemaker 512 and a distal opening 510 through which pacemaker 512 is loaded into delivery catheter 502 and released from delivery catheter 502 at an implant site. Outer delivery catheter 502 defines an outer lumen 527 that communicates with distal device receptacle 506. Advancement tool 518 extends through outer lumen 527.

Advancement tool 518 defines a middle lumen 516 and includes a distal cup or cone 515 configured to interface with the proximal end 514 of housing 550 for advancing housing 550 out distal opening 510 when advancement tool 518 is advanced distally through outer delivery catheter 502.

Inner steering tool 504 is an elongated tubular body that extends through middle lumen 516 defined by advancement tool 518. Inner steering tool 504 defines an inner lumen 505 through which steering member 580 extends. In some examples, inner steering tool 504 is a passive tubular body that follows the contour of advancement tool 518 and steering member 580. In other examples, as further described below in conjunction with FIGS. 9A through 9D, inner steering tool 504 is a steerable body that can be used in combination with steering member 580 to position proximal pacing electrode 532 at a pacing site. In the example shown, steering member 580 includes an engagement member configured as a loop 584 coupled to attachment member 570, configured as a post and rail similar to attachment member 370 of FIG. 6A. Advancement tool 518 and outer delivery catheter 502 are retractable and advanceable relative to inner steering tool 504. Before delivery tool 500 is advanced to an implant site within a patient, steering tool 504 may be advanced relative to advancement tool 518 and outer delivery catheter 502 (by either advancing steering tool 504 and/or retracting outer delivery catheter 502 and advancement tool 518) to expose a distal engagement member 584, also referred to herein as "loop" 584, of steering member 580. This allows steering member 580 to be attached to attachment member 570 of pacing extension 530 by positioning loop 584 over attachment member 570.

Once steering member 580 is coupled to proximal pacing extension 530, outer delivery catheter 502 and advancement tool 518 may be advanced relative to inner steering tool 504 (and/or steering tool 504 is retracted relative to delivery catheter 502 and advancement tool 518) to retract proximal pacing extension 530 proximally within middle lumen 516 of advancement tool 518 and position housing 550 and fixation member 540 of pacemaker 512 within receptacle 506. Steering body 582 of steering member 580 may be retracted from a proximal end (not illustrated in FIG. 8) to pull pacing extension 530 into a linear position, retracting pacing extension 530 into middle lumen 516, and mate housing proximal end 514 against distal cone 515 defined by advancement tool 518. Cone 515 is sized to mate with the housing proximal end 514 and may serve to center or guide tip electrode 532 and pacing extension fixation member 520 within middle lumen 516 to facilitate advancement and retraction of proximal pacing extension 530 into and out of middle lumen 516.

Figure 9:
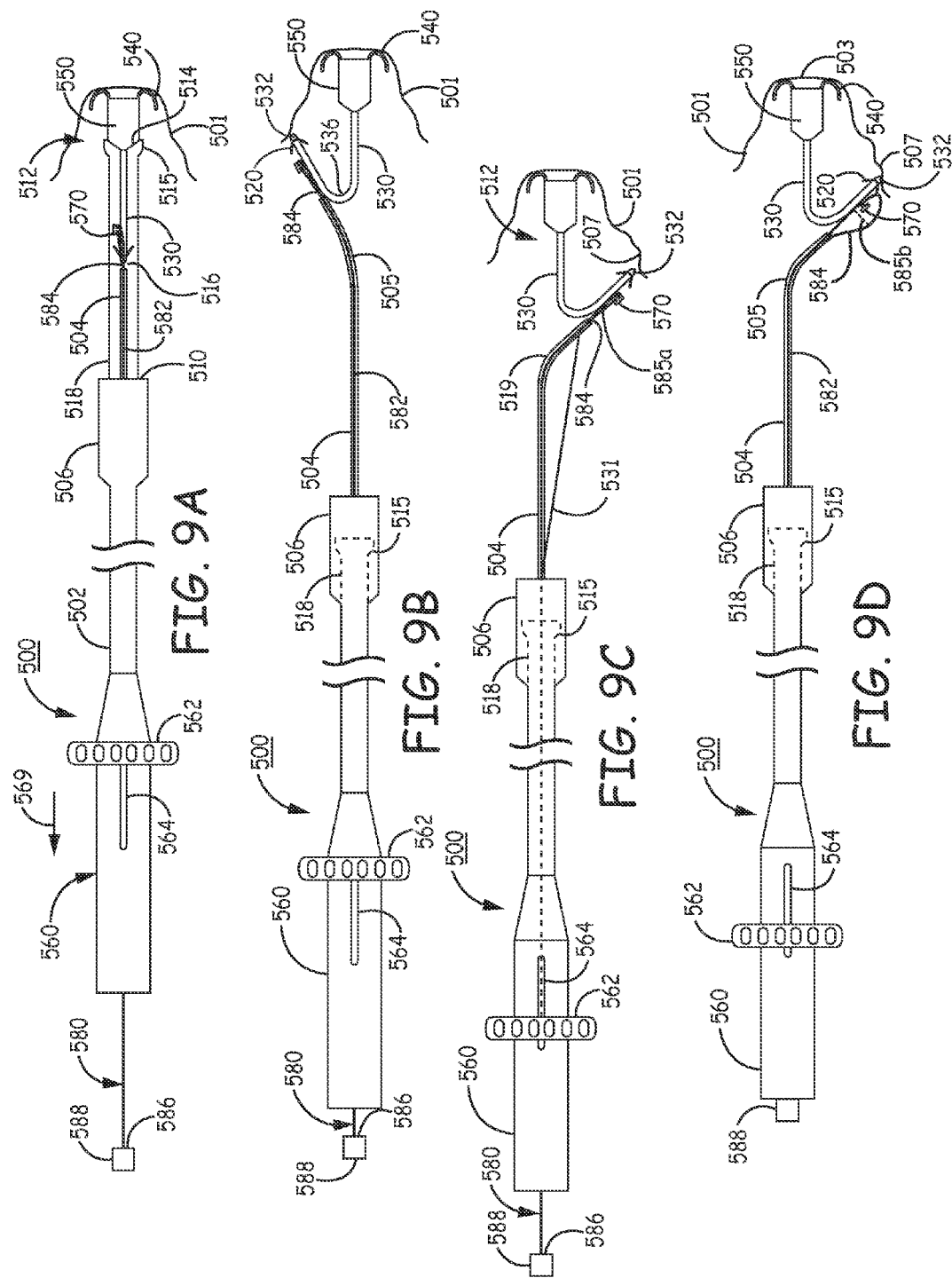
FIGS. 9A through 9D are conceptual diagrams of a delivery tool being used to deploy a pacemaker according to one example.

FIGS. 9A through 9D are conceptual diagrams of delivery tool 500 being used to deploy pacemaker 512 and steer proximal pacing extension 530 to position proximal pacing electrode 532 at a pacing site. In FIG. 9A, delivery tool 500 is shown to include a proximal handle 560. In this example, inner steering tool 504 is a steerable body. Handle 560 includes an actuating member 562 that is used to cause deflection of a distal portion 519 (as shown in FIG. 9C) of inner steering member 504. Actuating member 562 is advanced and retracted by a user along slot 564. Actuation member 562 is coupled to inner steering tool 504, for example by a pull wire. Retraction of actuating member 562 in a proximal direction causes the distal portion 519 of inner steering member 504 to bend or curve, e.g., as shown in FIGS. 9C and 9D. In one example, inner steering tool 504 includes a pull wire 531 shown schematically in FIG. 9C that has a proximal end coupled to actuating member 562 and a distal end coupled at or near a distal end of inner steering member 504. It is recognized that when inner steering tool 504 is a steerable member, it may include a pull wire or guide wire lumen through which the pull wire 531 may extend from the actuating member 562 to or near the distal end of inner steering tool 504. When actuating member 562 is moved proximally along slot 564 (in direction of arrow 569), the pull wire 531 causes bending of the distal portion 519 of inner steering tool 504.

In some examples, actuating member 562 may be rotatable. If rotated in one direction, e.g., clockwise, the position of actuating member 562 along slot 564 is locked. If rotated in an opposite direction, e.g., counterclockwise, the longitudinal position of actuating member 562 along slot 564 is unlocked and actuating member 562 is free to be advanced and retracted along slot 564.

Steering member 580 extends outward from proximal handle 560 to a steering member proximal end 586. Proximal end 586 may be configured with a handle or grip 588 to facilitate rotation and advancement and retraction of steering member 580 within inner steering tool 504.

In FIG. 9A, delivery catheter 502 has been retracted relative to inner steering tool 504 such that housing 550 and fixation member 540 are released from receptacle 506 at an implant site, e.g., within atrial appendage 501. After loading pacemaker 512 into delivery tool 500 as shown in FIG. 8, delivery tool 500 is advanced to a desired implant site, e.g., in the right atrial appendage 501. Distal opening 510 of outer delivery catheter 502 may be abutted against tissue at the implant site or positioned in very close proximity to a target implant site. Advancement tool 518 may be advanced and/or outer delivery catheter 502 may be retracted such that pacemaker 512 is held against an implant site by cone 515 of advancement tool 518, and housing 550 is released from receptacle 506 through distal opening 510.

Proximal pacing extension 530 is shown held in a linear position within middle lumen 516 of advancement tool 518 with steering member 580 retracted within inner steering tool 504. Steering member loop 584 is removably coupled around attachment member 570. Loop 584 is held in a taut position within steering member tool 504 such that an exposed portion of loop 584 is held tightly around attachment member 570.

In FIG. 9B, advancement tool 518 has been retracted and withdrawn into outer delivery catheter 502. Fixation member 540 moves from an extended position within receptacle 506 as shown in FIG. 8 to a relaxed or compressed position at the implant site within atrial appendage 501 and in so doing becomes engaged with tissue at the implant site. For example, fixation member 540 may become wedged in a compressed position between opposing tissue surfaces within the atrial appendage 501 such that opposing forces between fixation member 540 and opposing walls of atrial appendage 501 retain housing 550 within atrial appendage 501.

After fully deploying pacemaker 512 from advancement tool 518, pacing extension 530 resumes its relaxed position including any preformed curve 536 as shown in FIG. 9B. Proximal pacing electrode 532 may be held against tissue by a self-supporting pacing extension 530 and/or passive fixation member 520. Pacing capture threshold tests or other testing may be performed with proximal pacing electrode 532 at this initial candidate site.

The position of proximal pacing electrode 532 can be adjusted by retracting or rotating proximal grip 588 of steering member 580. By retracting proximal grip 588 a pulling force is applied to attachment member 570 causing deflection or straightening of pacing extension 530. By rotating proximal grip 588, steering member 580 may translate torque along the length of steering member body 582 and thereby cause lateral movement of tip electrode 532 along the tissue to various candidate pacing sites.

Additionally or alternatively, when steering tool 504 is a steerable tool, the position of proximal pacing electrode 532 can be adjusted as needed by retracting actuating member 506 along slot 564 as shown in FIG. 9C. By retracting actuating member 562, distal portion 519 of inner steering tool 504 is deflected, e.g., by pull wire 531, effectively "picking up" pacing extension 530 or lifting away proximal pacing electrode 532 from a tissue site. Inner steering tool 504 may be rotatable at its proximal end in some examples to enable directional steering of the deflected distal end of inner steering tool 504. Steering member 580 maintains connection between inner steering tool 504 and pacing extension 530 to enable this manipulation of pacing extension 530 to position proximal pacing electrode 532 at a new pacing site 507. Additionally, rotation of steering member 580 at its proximal end 586 may contribute to the steering of pacing extension 530.

After selecting a pacing site 507 steering member 580 is advanced distally through inner steering tool 504, by advancing steering member proximal end 586 into handle 560 as shown in FIG. 9D. The proximal grip 588 may act as a stop to prevent over-extension of steering member 580. Upon advancement of steering member 580, steering member distal loop 584 is advanced outward from the distal end of inner steering tool 504. When at least partially retracted and constrained within lumen 505 of inner steering tool 504, e.g., as shown in FIG. 9C, steering member distal loop 584 is held taut in a collapsed, elongated or closed position such that its open circumference 585a is smaller than an outer dimension of attachment member 570. In this way, distal loop 584 is held in a securely around attachment member 570. When steering member 580 is advanced distally such that distal loop 584 extends out of inner lumen 505 and is unconstrained by lumen 505 of inner steering tool 504, it is free to open into a relaxed open position having an open circumference 585b that enables loop 584 to easily slip over and away from attachment member 570.

Once released from attachment member 570, steering member 580 may be retracted into lumen 505 of inner steering tool 504. Delivery tool 500 may then be withdrawn from the patient leaving pacemaker 512 implanted with housing 550 anchored at an implant site 503 by fixation member 540 and proximal pacing electrode 532 anchored at a pacing site 507 spaced apart from housing implant site 503. In the example shown, the position of proximal pacing electrode 532 is maintained by self-supporting pacing extension 530 and proximal fixation member 520. In other embodiments, pacing extension 530 is flexible and proximal pacing electrode 532 is anchored at pacing site 507 by proximal fixation member 520.

Figure 10:
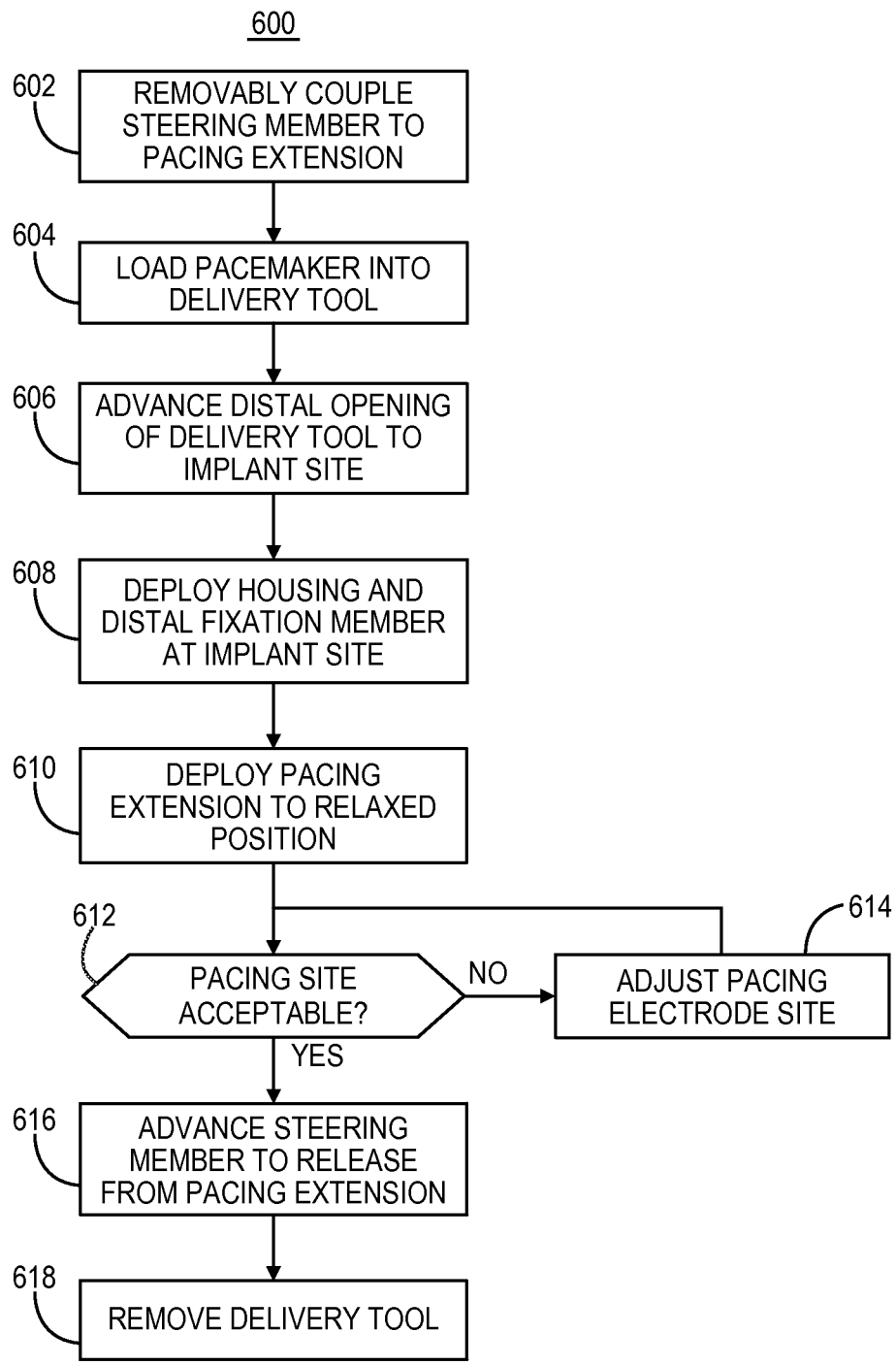
FIG. 10 is a flow chart of a method for deploying an intracardiac pacemaker having a proximal pacing extension according to one example.

FIG. 10 is a flow chart 600 of a method for deploying an intracardiac pacemaker, such as pacemaker 512 of FIGS. 9A-9D, having a proximal pacing extension according to one example. With reference to delivery tool 500 and pacemaker 512, at block 602 steering member 580 of delivery tool 500 is removably coupled to a proximal pacing extension 530 of the intracardiac pacemaker 512. According to the various examples described herein, an engagement member of the steering member is removably coupled to the attachment member of the pacing extension 530. The engagement member may include a snare-type loop 584 that tightens around a rail of an attachment member 570 (e.g., as in FIG. 6A or 9C) or a tethering loop that extends through a loop-type attachment member 470 as in FIG. 7B.

At block 604, the intracardiac pacemaker 512 is loaded into the delivery tool such that the proximal pacing extension 530 extends proximally through a lumen of an advancement tool and the pacemaker housing 550 is retained by a distal receptacle 506 of the outer delivery catheter 502. The delivery tool 500 is advanced to an implant site at block 606. In some examples, outer delivery catheter 502 is a steerable catheter. In other examples, an outer guide tube may be advanced to a target implant site, e.g., over a stylet which is advance first and then removed so that delivery tool 500 can be advanced through the outer guide tube to the target implant site. The outer guide tube is then retracted and withdrawn leaving delivery tool 500 advanced to the target implant site.

Once distal opening 510 is positioned at a target implant site, the outer delivery catheter 502 is retracted (and/or advancement tool 518 is advanced) at block 608 to deploy the pacemaker housing 550 and a distal fixation member 540 to anchor the housing 550 at the implant site. At block 610, the proximal pacing extension is deployed from the delivery tool 500 as the pacemaker 512 is released from the advancement tool 518 and assumes a relaxed position such that the proximal pacing electrode 532 carried by the pacing extension 530 is positioned at a candidate pacing site. Testing may be performed at the candidate pacing site and/or imaging may be performed to verify that the site is acceptable at block 612. If the candidate pacing site is unacceptable, the proximal pacing electrode 532 is adjusted to a new candidate site at block 614.

As described in conjunction with FIGS. 9A-9D, inner steering tool 504 and/or delivery tool steering member 580 coupled to the proximal pacing extension 530 may be manipulated at a proximal handle end of the delivery tool 500 to adjust the position of the proximal pacing electrode 532. Additionally or alternatively, the pacemaker 512 may be recaptured at block 614 by retracting on the steering member 580 to pull steering member body 582 and a portion of engagement member loop 584 (still coupled to attachment member 570) back into inner lumen 505. As steering member 580 is retracted, proximal pacing extension 530 is pulled into a straightened position and can be retracted back into middle lumen 516 of advancement tool 518. Advancement tool 518 may be advanced over inner steering tool 504 to position cone 515 against housing proximal end 514. Outer delivery catheter 502 is then advanced over advancement tool 518, recapturing housing 550 by cone 515 and receptacle 506. Delivery tool 500 may then be advanced to a new location so that the housing 550 and proximal pacing electrode 532 of pacemaker 512 may be redeployed at a new implant site and new candidate pacing site, respectively.

Once an acceptable pacing site is identified at block 612, the inner steering member 580 is advanced through the inner steering tool 504 to open and release the engagement member loop 584 of the steering member 580 from the proximal pacing extension attachment member 570 at block 616. For example, a proximal end 586 of the steering member 580 may be advanced distally at a proximal handle end to release the engagement member loop 584 from the attachment member 570, e.g., by enlarging loop 584 of the steering member 580 (see FIGS. 6B and 9D). In other embodiments, the steering member is released from the attachment member by pulling one proximal end of the steering member all the way through a loop-type attachment member 470 (see FIG. 7C).

After uncoupling the steering member 580 from the proximal pacing extension attachment member 570, the delivery tool 500 may be withdrawn from the patient at block 618. The pacemaker 512 is left implanted in the patient's heart chamber with the housing 550 fixed at an implant site by the distal fixation member 540 and the proximal pacing electrode 532 positioned at a pacing site spaced apart from the implant site.

Thus, various embodiments and methods for use of an intracardiac pacemaker having a proximal pacing extension have been described. Various aspects of the illustrative examples described herein and shown in the accompanying drawings may be combined in different combinations than the particular combinations shown. It is recognized that various modifications may be made to the described embodiments without departing from the scope of the following claims.

The invention claimed is:

1. An implantable pacemaker system, comprising:
   a housing having a proximal end and a distal end and comprising:
      a control electronics subassembly defining the housing proximal end; and
      a battery subassembly defining the housing distal end;
   a distal fixation member extending from the housing distal end for fixing the housing distal end at an implant site;
   a pacing extension extending from the housing proximal end and comprising an electrical conductor; and
   a pacing cathode electrode carried by the pacing extension to position the pacing cathode electrode at a pacing site that is spaced apart from the implant site when the pacemaker is deployed in a patient's body, the pacing cathode electrode electrically coupled to the control electronics assembly via the pacing extension electrical conductor.

2. The system of claim 1, further comprising a proximal fixation member extending from the pacing extension for anchoring the pacing cathode electrode at the pacing site.

3. The system of claim 1, wherein the distal fixation member is a passive fixation member.

4. The system of claim 1, wherein the pacing extension comprises an attachment member for receiving a steering member.

5. The system of claim 4, wherein the attachment member comprises at least one of a post, a rail, a loop and a hook for engaging a loop of the steering member.

6. The system of claim 1, wherein:
   the distal fixation member comprises a fixation ring and a plurality of fixation tines extending from the fixation ring;
   the housing distal end comprises:
      a battery subassembly distal face;
      a mating member along the distal battery face; and
      a distal cap configured to mate with the mating member;
   the fixation ring captured between the distal cap and the battery subassembly distal face.

7. The system of claim 1, further comprising an anode ring electrode carried along one of the housing and the pacing extension and is spaced apart from the implant site when the pacemaker is deployed in the patient's body.

8. The system of claim 1, further comprising:
an attachment member extending from the pacing extension; and
an elongated delivery tool comprising:
an outer delivery catheter defining an outer lumen and an open distal end for receiving the pacing extension and the housing;
an inner steering tool extending through the outer delivery catheter, the inner steering tool defining an inner lumen and having a distal end; and
a steering member extending through the inner steering tool and configured to be removably coupled to the attachment member.

9. The system of claim 8, wherein the elongated delivery tool further comprises a proximal handle comprising an actuating member for causing deflection of the inner steering tool distal end to cause movement of the pacing extension via the steering member coupled to the attachment member.

10. The system of claim 8, wherein the steering member comprises a proximal end extending from the proximal handle and a loop that is removably coupled to the attachment member, the steering member loop being removable from the attachment member by advancement of the proximal end of the steering member through inner steering tool lumen.

11. A method for using an implantable pacemaker system, comprising:
deploying at an implant site a pacemaker housing having a proximal end and a distal end and comprising a control electronics subassembly defining the housing proximal end and a battery subassembly defining the housing distal end;
deploying a distal fixation member extending from the housing distal end for fixing the housing distal end at the implant site; and
deploying a pacing extension extending from the housing proximal end and comprising an electrical conductor and a pacing cathode electrode carried by the pacing extension to position the pacing cathode electrode at a pacing site that is spaced apart from the implant site, the pacing cathode electrode electrically coupled to the control electronics assembly via the pacing extension electrical conductor.

12. The method of claim 10, further comprising deploying a proximal fixation member extending from the pacing extension to anchor the pacing cathode electrode at the pacing site.

13. The method of claim 1, wherein deploying the distal fixation member comprises releasing the distal fixation member from a delivery tool to passively engage tissue at the implant site.

14. The method of claim 11, further comprising coupling a steering member to an attachment member of the pacing extension.

15. The method of claim 14, wherein coupling the steering member to the attachment member comprises engaging a loop of the steering member with the attachment member, wherein the attachment member comprises at least one of a post, a rail, a loop and a hook.

16. The method of claim 11, further comprising delivering pacing pulses to a patient's heart between the cathode pacing electrode and a return anode electrode carried along one of the housing and the pacing extension spaced apart from the implant site.

17. The method of claim 11, further comprising:
removably coupling a steering member to an attachment member extending from the pacing extension, the steering member extending through an inner lumen defined by an inner steering tool of an elongated delivery tool;
wherein deploying the housing comprises:
loading the housing and the pacing extension in a delivery catheter of the elongated delivery tool:
advancing the elongated delivery tool to the implant site;
retracting the delivery catheter to release the housing, the distal fixation member and the pacing extension out a distal opening of the delivery tool;
wherein deploying the pacing extension comprises adjusting a position of the pacing cathode electrode by manipulating a proximal end of the steering member.

18. The method of claim 17, wherein deploying the pacing extension further comprises manipulating an actuating member for causing deflection of an inner steering tool distal end to cause movement of the pacing extension via the steering member coupled to the attachment member and extending through the inner steering tool, the actuating member movable along a proximal handle of the delivery tool.

19. The method of claim 17, further comprising removing the steering member by advancing a proximal end of the steering member through inner steering tool lumen.

20. The method of claim 12, wherein deploying the distal fixation member comprises wedging the distal fixation member within an atrial appendage.

21. A pacemaker system comprising:
an intracardiac pacemaker comprising:
a housing having a proximal end and a distal end and comprising:
a control electronics subassembly defining the housing proximal end; and
a battery subassembly defining the housing distal end;
a distal fixation member extending from the housing distal end for fixing the housing distal end at an implant site;
a pacing extension extending from the housing proximal end and comprising an electrical conductor; and
a pacing cathode electrode carried by the pacing extension to position the pacing cathode electrode at a pacing site that is spaced apart from the implant site when the pacemaker is deployed in a patient's body, the pacing cathode electrode electrically coupled to the control electronics assembly via the pacing extension electrical conductor; and
a delivery tool comprising:
a delivery catheter defining a receptacle for receiving the intracardiac pacemaker and an outer lumen;
an inner steering tool extending through the outer lumen and defining an inner lumen;
a steering member extending through the inner lumen and comprising an engagement member for coupling to the pacing extension for retracting the pacing extension during a surgical procedure.

22. An implantable pacemaker system, comprising:
a housing having a proximal end and a distal end and comprising:
a control electronics subassembly defining the housing proximal end; and
a battery subassembly defining the housing distal end;
a distal fixation member subassembly configured to mate with the housing distal end, the distal fixation member subassembly comprising a polymer fixation member having multiple tines extending from the housing distal end for fixing the housing distal end at an implant site in a heart chamber and a mating member for coupling the fixation member to the housing distal end;

a pacing extension having a proximal tip, the pacing extension comprising an elongated body extending from the housing proximal end to the proximal tip of the pacing extension and comprising an electrical conductor extending through the elongated body;

a pacing cathode electrode carried by the pacing extension proximal tip to position the pacing cathode electrode at a pacing site in the heart chamber that is spaced apart from the implant site when the pacemaker is deployed in the heart chamber, the pacing cathode electrode electrically coupled to the control electronics subassembly via the pacing extension electrical conductor; and an attachment member along the elongated body configured to be removably coupled to a steering member for steering the pacing cathode electrode to the pacing site, the attachment member being spaced apart distally along the elongated body from the pacing cathode electrode.

\* \* \* \* \*